United States Patent [19]

Laundon

[11] 4,076,936
[45] Feb. 28, 1978

[54] 7β-(2-ARYL-2-HYDROX-YIMINOACETAMIDO)CEPH-3-EM-4-CARBOXYLIC ACIDS CARRYING A 7α-LOWER ALKOXY SUBSTITUENT

[75] Inventor: Brian Laundon, Grange-over-Sands, England

[73] Assignee: Glaxo Laboratories Limited, Greenford, England

[21] Appl. No.: 746,596

[22] Filed: Dec. 1, 1976

Related U.S. Application Data

[62] Division of Ser. No. 485,233, Jul. 1, 1974, Pat. No. 4,007,174.

[30] Foreign Application Priority Data

Jul. 6, 1973    United Kingdom ............... 32273/73

[51] Int. Cl.² ................. C07D 501/20; A61K 31/545
[52] U.S. Cl. ....................................... 544/21; 424/246
[58] Field of Search ...................... 260/243 C; 544/21

[56] References Cited

U.S. PATENT DOCUMENTS 3,962,224    6/1976    Christensen et al. ............ 260/243 C Primary Examiner—Nicholas S. Rizzo
Attorney, Agent, or Firm—Bacon & Thomas

[57] ABSTRACT

Novel syn-7β-(2-aryl-2-hydroxyiminoacetamido)ceph-3-em-4-carboxylic acids carrying a 7α-lower alkoxy substituent, particularly a 7α-methoxy group, which are broad spectrum antibiotics exhibiting low serum binding are described.

4 Claims, No Drawings

7β-(2-ARYL-2-HYDROXYIMINOACETAMIDO)-CEPH-3-EM-4-CARBOXYLIC ACIDS CARRYING A 7α-LOWER ALKOXY SUBSTITUENT

This is a division of application Ser. No. 485,233, filed July 1, 1974 now U.S. Pat. No. 4,007,174.

This invention is concerned with improvements in or relating to antibiotics of the cephalosporin series.

The cephalosporin compounds referred to in this specification are generally named with reference to cepham (J. Amer. Chem. Soc. 1962, 84, 3400). The term "cephem" refers to the basic cepham structure with one double bond.

As is well known, antibiotics of the cephalosporin series comprise 7β-acylamido-ceph-3-em-4-carboxylic acids and their various non-toxic derivatives e.g. salts, esters, lactones (if such can be formed), amides, hydrates or the corresponding sulphoxides. These antibiotics may contain various substituents, particularly at the 3-position, including unsubstituted methyl and methyl groups substituted with a variety of substituents as is described in the literature.

One known class of cephalosporin antibiotics comprises compounds in which the 7β-acylamido group is substituted in the α-position by a hydroxyimino group; we have now found that certain 7α-substituted analogues of such cephalosporin oximes, namely compounds carrying a lower alkoxy group at the 7α-position, exhibit valuable antibiotic properties, possessing activity against a range of gram positive and gram negative organisms coupled with low serum binding.

Thus according to one aspect of the present invention we provide a compound which comprises a 7β-(2-aryl-2-hydroxyiminoacylamido)ceph-3-em-4-carboxylic acid or a non-toxic derivative thereof characterised in that the compound is substituted at the 7α-position by a lower (i.e. $C_{1-4}$) alkoxy group.

The compounds of the invention thus include compounds of the general formula

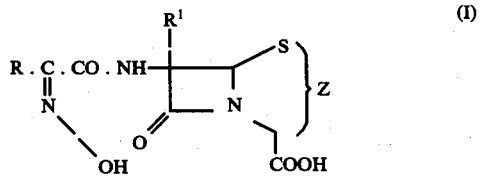

(I)

[wherein R is an aryl group (carbocyclic or heterocyclic) $R^1$ is a $C_{1-4}$ alkoxy group; and Z is a group in which 2 carbon atoms link the nuclear sulphur atom and the carbon atom bearing the carboxylic acid group so that the compound possesses $\Delta^3$ unsaturation] and non-toxic derivatives thereof. The compounds exist as syn (cis) isomers as regards the configuration of the hydroxyimino group = N $\sim$ OH with respect to the carboxamido group, and may be prepared either in substantially pure isomeric form or as mixtures of isomers. Mixtures of isomers should contain at least 75%, preferably at least 90% of the syn isomer, and for many applications it will be perferred to use the compound in substantially pure isomeric form.

In this specification the syn configuration is structurally denoted thus:

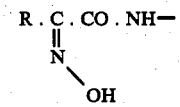

This configuration is assigned on the basis of the work of Ahmad and Spenser reported in Can. J. Chem., 1961, 39, 1340.

By the term "non-toxic derivatives" as used herein in relation to the compounds of the invention we mean derivatives such as salts, esters, lactones (where such can be formed), amides and hydrates which are physiologically acceptable in the dosage at which they are administered.

Salts which may be formed, where applicable, from the compounds according to the invention include (a) inorganic base salts such as alkali metal, e.g. sodium and potassium, alkaline earth metal e.g. calcium, and organic base, e.g. procaine, phenylethylbenzylamine and dibenzylethylene diamine, salts and (b) acid addition salts, e.g. with hydrochloric, hydrobromic, sulphuric, nitric, phosphoric, toluene-p-sulphonic and methane sulphonic acids. The salts may also be in the form of resinates, formed with, for example, a polystyrene resin or cross-linked polystyrene divinyl-benzene copolymer resin containing amino, quaternary amino, or sulphonic acid groups, or with a resin containing carboxyl groups, e.g. a polyacrylic acid resin.

Compounds of particular interest according to the invention include those represented by the structural formula

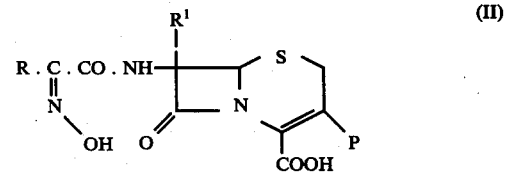

(II)

(wherein R and $R^1$ have the above-defined meanings and P is an organic group) and non-toxic derivatives thereof. (It should be understood that structural formula II includes compounds such as 2-methyl, 2-methylene, 2-methoxy, 2-benzyl and 2-benzylidene cephalosporins which are not specifically embraced thereby).

The group R in the above general formulae may be chosen from phenyl; naphthyl e.g. naphth-1-yl; phenyl or naphthyl substituted by halo e.g. chloro or bromo as in o-chlorophenyl, hydroxy, lower alkyl e.g. methyl, nitro, amino, lower alkylamino e.g. methylamino, diloweralkylamino e.g. dimethylamino, lower alkanoyl e.g. acetyl, lower alkanoylamido, lower alkoxy e.g. methoxy or ethoxy, or lower alkylthio e.g. methylthio; a 5- or 6-membered heterocyclic group containing at least one hetero atom selected from S, N and O e.g. thien-2-yl, thien-3-yl, furyl such as fur-2-yl, pyridyl such as pyrid-3-yl, pyrrolyl, N-substituted pyrrolyl e.g. N-methylpyrrolyl, isothiazolyl, thiadiazolyl, oxadiazolyl, 3- or 4-isoxazolyl; substituted 3- or 4-isoxazolyl e.g. 3-aryl-5-methylisoxazol-4-yl, the aryl group being e.g. phenyl or halophenyl; fused heterocyclic groups containing at least one hetero atom selected from S, N and O, e.g. benzothienyl such as benzothien-3-yl, benzofuryl and indolyl.

The alkyl portion of the group $R^1$ present at the 7α-position of the compounds according to the invention may be straight or branched. Examples of 7α-substituents thus include methoxy, ethoxy, n-propoxy and iso-propoxy. Preferably the group is methoxy.

The 3-substituent P in formula II may be any organic group, the characterising feature of the invention being the nature of the 7-substituents. P may thus be a saturated or unsaturated, substituted or unsubstituted, organic group containing 1-20 carbon atoms. Saturated organic groups include methyl and ethyl; unsaturated organic groups include vinyl and substituted vinyl groups of the formula

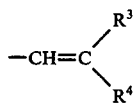

wherein $R^3$ and $R^4$, which may be the same or different, are each hydrogen or a substituted or unsubstituted aliphatic (e.g. alkyl, preferably $C_1$-$C_6$ alkyl such as methyl, ethyl, iso-propyl n-propyl etc.), $C_5$-$C_7$ cycloaliphatic (e.g. cyclopentyl or cyclohexyl), $C_7$-$C_{10}$ araliphatic (e.g. benzyl or phenylethyl), $C_6$-$C_{12}$ aromatic (e.g. phenyl or nitrophenyl) group, nitrile or lower alkoxycarbonyl.

When P is a substituted methyl group it may be depicted by the formula $$-CH_2Y$$

wherein Y is an atom or group e.g. the residue of a nucleophile or a derivative of a residue of a nucleophile. Y may thus, for example, be derived from the wide range of nucleophilic substances characterised by possessing a nucleophilic nitrogen, carbon, sulphur or oxygen atom described widely in earlier patents and literature pertaining to cephalosporin chemistry. Examples of such nucleophiles include:

NITROGEN NUCLEOPHILES

Examples of nitrogen nucleophiles include tertiary aliphatic, aromatic, araliphatic and cyclic amines including trialkylamines, for example, triethylamine, pyridine bases such as pyridine and alkyl pyridines; heterocyclic amines having more than one heteroatom, at least one heteroatom being nitrogen, such as pyrimidines, purines, pyridazines, pyrazines, pyrazoles, imidazoles, triazoles and thiazoles.

One class of nitrogen nucleophiles comprises compounds of the formula:

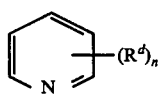

in which $n$ is 0 or an integer from 1 to 5 and $R^d$, which when $n$ is from 2 to 5, may be the same or different, is an aliphatic, e.g. lower alkyl such as methyl, ethyl, n-propyl, iso-propyl etc; an aryl e.g. phenyl; an araliphatic, e.g. phenyl lower alkyl such as benzyl, phenylethyl etc; or an alkoxymethyl e.g. methoxymethyl, ethoxymethyl, n-propoxymethyl, iso-propoxymethyl etc; or acyloxymethyl e.g. alkanoyloxymethyl such as acetoxymethyl; formyl; carbamoyl; acyloxy e.g. alkanoyloxy such as acetoxy; esterified carboxyl; alkoxy e.g. methoxy, ethoxy, n-propoxy, iso-propoxy etc; aryloxy e.g. phenoxy; aralkoxy e.g. benzyloxy; alkylthio e.g. methyl-thio, ethylthio; arylthio; aralkylthio; cyano; hydroxy; N-monoloweralkylcarbamoyl e.g. N-methylcarbamoyl, N-ethylcarbamoyl etc; N,N-diloweralkylcarbamoyl e.g. N,N-dimethylcarbamoyl, N,N-diethylcarbamoyl etc; N-(hydroxyloweralkyl)carbamoyl e.g. N-(hydroxymethyl)carbamoyl, N-(hydroxyethyl)carbamoyl etc; or carbamoylloweralkyl e.g. carbamoylmethyl, carbamoylethyl etc. group. An example of a nucleophile of this type is 4-carbamoylpyrid-1-yl.

Another class of nitrogen nucleophiles comprises azides, e.g. alkali metal azides such as sodium azide.

When the group Y is a derivative of a residue of a nucleophile it may be an amino group or an acylamido group. Compounds in which Y is amino may be derived from the corresponding azide by reduction e.g. by catalytic hydrogenation of the azide using a precious metal catalyst such as palladium or platinum.

The amino group may be acylated to form a corresponding 3-acylaminomethyl compound. The formation of such compounds may, for example, be effected by any method suitable for acylating an aminocephalosporin e.g. reaction of the 3-aminomethyl compound with an acid chloride, acid anhydride or mixed anhydride or an acid corresponding to the desired acyl group and another acid.

The 3-aminomethyl compounds may also be reacted with a substituted isocyanate or isothiocyanate to yield urea of thiourea derivatives.

Other compounds in which Y is a derivative of a residue of a nucleophile may be obtained by reacting 3-azidomethyl compounds with a dipolarophile. Examples of suitable dipolarophiles include acetylenic, ethylenic and cyano dipolarophiles.

Acetylenic dipolarophiles may be shown as having the structure $$R^1.C{\equiv}C.R^2$$

wherein $R^1$ and $R^2$ which may be the same or different are atoms or groups.

In general we prefer that $R^1$ and preferably also $R^2$ should be of an electronegative nature. Examples of such groups include cyano, $CO_2R^3$, $COR^3$ (where $R^3$ is for example, lower alkyl, aryl or lower aralkyl), and trihalomethyl e.g. trifluoromethyl.

$R^1$ and $R^2$ may together form a ring system with the acetylenic group such as, for example, in an aryne.

Where $R^1$ and $R^2$ are discrete atoms or groups which are identical a single compound will result on reaction with the azido cephalosporin; if they are different one will in general obtain a mixture of position isomers.

Ethylenic dipolarophiles may be shown as having the structure

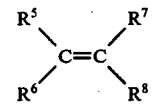

where $R^5$, $R^6$, $R^7$ and $R^8$ which may be the same or different are atoms or groups. Although $R^5$, $R^6$, $R^7$ and $R^8$ may all be hydrogen, ethylene per se, like acetylene, reacts sluggishly with azide groups. $R^5$ and $R^7$ may together form a cyclic structure, e.g. a carbocylic structure, with the ethenoid group such that the double bond is strained. Examples of ethylenic dipolarophiles containing strained double bonds include norbornenes, transcycloalkenes and acenaphthalene.

Further ethylenic dipolarophiles which may be used include compounds of the formula $R^5.R^6.C = CR^7.R^8$ where at least one of $R^5$, $R^6$, $R^7$ and $R^8$ is an electronegative group. $R^5$ and $R^7$ may thus be identical electronegative groups, $R^6$ and $R^8$ being other groups as desired. $R^6$ and $R^8$ may thus together form a ring system. Examples of such dipolarophiles include benzoquinone and nuclear substituted benzoquinones and maleimide. Again all of $R^5$, $R^6$, $R^7$ and $R^8$ may be identical electronegative groups. Electronegative groups which may be used include those listed under the section on acetylenic dipolarphiles and examples of such compounds thus include dicyanoethylene and lower mono- and di-alkoxycarbonyl ethylenes.

One or more of $R^5$, $R^6$, $R^7$ and $R^8$ may if desired be electropositive.

Cyano compounds, especially those which are activated by electronegative groups, may function as cyano dipolarophiles. Examples of such dipolarophiles include lower alkoxy carbonyl cyanides and cyanogen.

CARBON NUCLEOPHILES

Examples of "carbon nucleophiles" include inorganic cyanides, pyrroles and substituted pyrroles, e.g. indoles, and compounds giving stabilized carbanions, for example, acetylenes and compounds having $\beta$-diketone groups, for example acetoacetic and malonic esters and cyclohexane-1,3-diones or enamines, ynamines or enols.

The carbon nucleophile may thus give rise to cephalosporin compounds characterized by possessing a substituent at the 3-position in which a carbonyl group is linked to the cephalosporin nucleus through two carbon atoms. Such compounds may thus possess as the 3-substituent a group of the formula

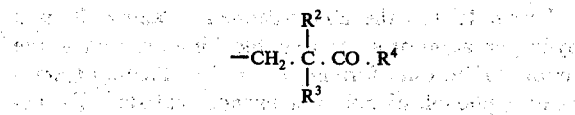

wherein $R^2$ and $R^3$, which may be the same or different, are selected from hydrogen, cyano, lower alkyl e.g. methyl or ethyl, phenyl, substituted phenyl e.g. halo, lower alkyl, lower alkoxy, nitro, amino or lower alkylamino phenyl, lower alkoxycabonyl, mono- or di-aryl lower alkoxycarbonyl, lower alkylcarbonyl, aryl lowr alkyl or $C_5$ or $C_6$ cycloalkyl and $R^4$ is selected from hydrogen, lower alkyl e.g. methyl or ethyl, phenyl, substituted phenyl e.g. halo, lower alkyl, lower alkoxy, nitro, amino or lower alkylamino phenyl, aryl lower alkyl or $C_5$ or $C_6$ cycloalkyl.

SULPHUR NUCLEOPHILES

Examples of "sulphur nucleophiles" include thiourea and aliphatic, aromatic, araliphatic, alicylic and heterocyclic substituted thioureas; dithiocarbamates; aromatic, aliphatic and cyclic thioamides, for example thioacetamide and thiosemicarbazide; thiosulphates; thiols; thiophenols; thioacids, e.g. thiobenzoic acid or thiopicolinic acid; and dithioacids.

One class of "sulphur nucleophile" includes those compounds of the formula: $R^1.S(O)_nH$ in which $R^1$ is an aliphatic e.g. lower alkyl such as methyl, ethyl, n-propyl etc. group; an alicyclic e.g. cyclohexyl, cyclopentyl etc. group; an aromatic e.g. phenyl, naphthyl etc. group; an araliphatic e.g. benzyl group; or a heterocyclic group, and n is 0, 1 or 2. A preferred class of nucleophiles falling within the above formula is that having the general formula: $R^6SH$ in which $R^6$ is aliphatic e.g. lower alkyl such as methyl, ethyl, n-propyl etc. or lower alkanoyl such as acetyl; araliphatic, e.g. phenyl lower alkyl such as benzyl, phenethyl etc. or substituted phenyl lower alkyl; alicyclic e.g. cycloalkyl such as cyclopentyl or cyclohexyl; aromatic e.g. phenyl, substituted phenyl, or a heterocyclic group containing at least one 5- or 6-membered ring and having one or more heteroatoms selected from O, N and S. Such heterocyclic groups $R^6$ may be substituted, and examples of suitable heterocyclic groups include thiadiazolyl, e.g. 5-methyl-1,3,4-thiadiazol-2-yl; diazolyl; triazolyl; tetrazolyl, e.g. 1-methyltetrazol-5-yl, 1-ethyltetrazol-5-yl or 1-phenyltetrazol-5-yl; thiazolyl; thiatriazolyl; oxazolyl; oxadiazolyl, e.g. 2-phenyl-1,3,4-oxadiazol-5-yl; pyridyl; pyrimidyl; fused heretocyclic ring systems such as benzimidazolyl, benzoxazolyl, benzothiazolyl, triazolopyridyl or purinyl; and substituted versions of such fused ring systems, e.g. nitrobenzothiazol-2-yl such as 5- or 6-nitrobenzothiazol-2-yl.

OXYGEN NUCLEOPHILES

Examples of oxygen nucleophiles include water, alcohols, for example alkanols such as methanol, ethanol, propanol and butanol and lower alkanoic and alkenoic acids.

The term "oxygen nucleophile" thus includes compounds of the following formula:

$$R'OH$$

in which the group $R'$ may be lower alkyl (e.g. methyl, ethyl, n-propyl, isopropyl, n-butyl, isobutyl etc.); lower alkenyl (e.g. allyl); lower alkynyl (e.g. propynyl, etc); lower cycloalkyl (e.g. cyclopropyl, cyclopentyl, cyclohexyl, etc); lower cycloalkyl lower alkyl (e.g. cyclopropylmethyl, cyclopentylmethyl, cyclohexylethyl etc); aryl (e.g. phenyl or naphthyl); aryl lower alkyl (e.g. benzyl); heterocyclic; heterocyclic lower alkyl (e.g. furfuryl) or any of these groups substituted by, for example, one or more of lower alkoxy (methoxy, ethoxy, etc.), lower alkylthio (methylthio, ethylthio, etc), halogen (chlorine, bromine, iodine or fluorine), lower alkyl (methyl, ethyl etc), nitro, hydroxy, acyloxy, carboxy, carbalkoxy, lower alkylcarbonyl, lower alkylsulphonyl, lower alkoxysulphonyl, amino, lower alkylamino or acylamino groups.

In the case in which water is the nucleophile there will be obtained 3-hydroxymethyl cephalosporin compounds. Such 3-hydroxymethyl compounds and nontoxic derivatives thereof may show antibacterial activity and it is of note that they may be metabolites of compounds of general formula II where P is acetoxymethyl 3-Hydroxymethyl cephalosporins may be acylated to form derivatives characterized by possessing the group 3-$CH_2$.O.CO.$R^9$ or 3-$CH_2$.O.CO.$AR^{10}$ where A is O, S or Ni, $R^9$ is methyl or an organic group having an atomic weight sum of at least 16 and $R^{10}$ is hydrogen or $R^9$.

The group $R^9CO-$ or, $R^{10}A.CO-$ may be chosen from among the wide class of such groups described in the literature and may have up to 20 carbon atoms. The group $R^9$ may thus be a hydrocarbon group or such a group carrying one or more substituent atoms or groups. The group $R^9$ may thus be chosen from the following list which is not intended to be exhaustive:

(i) $C_nH_{2n+1}$ where $n$ is an integer from 1 to 7, e.g. 2 to 4. The group may be straight or branched and, if desired, may be interrupted by an oxygen or sulphur atom or an imino group or substituted by cyano, carboxy, alkoxycarbonyl, hydroxy, carboxycarbonyl (HOOC.CO.) halogen e.g. chlorine, bromine or iodine, or amino. Examples of such groups include ethyl, propyl, isopropyl, n-butyl, t-butyl, sec. butyl and 2-chloroethyl.

(ii) $C_nH_{2n-1}$ where $n$ is an integer from 2 to 7. The group may be straight or branched and, if desired, may be interrupted by an oxygen or sulphur atom or an imino group. Examples of such groups include vinyl and propenyl.

(iii) $R^y$, where $R^y$ is aryl (carbocyclic or heterocyclic), cycloalkyl, substituted aryl and substituted cycloalkyl. Examples of this group include phenyl; substituted phenyl e.g. hydroxyphenyl, chlorophenyl, fluorophenyl, tolyl, nitrophenyl, aminophenyl, methoxyphenyl or methylthiophenyl; thien-2- and -3-yl; pyridyl; cyclohexyl; cyclopentyl; cyclopropyl; sydnone; naphthyl; substituted naphthyl e.g. 2-ethoxynaphthyl.

(iv) $R^y(CH_2)_m$ where $R^y$ has the meaning defined above under (iii) and $m$ is an integer from 1 to 4. Examples of this group include methyl, ethyl or butyl substituted by the various specific $R^y$ groups listed under (iii) e.g. benzyl and the appropriate substituted benzyl groups.

3-Position substituents of the above type thus include lower alkanoyloxymethyl groups such as acetoxymethyl and isobutyryloxymethyl, lower alkenoyloxymethyl groups such as crotonyloxymethyl, and N-(haloalkyl)carbamoyloxymethyl such as N-(2-chloroethyl)carbamoyloxymethyl.

A further important class of cephalosporin compounds are those possessing the group 3-CH₂Hal wherein Hal is chlorine, bromine or iodine. Such compounds may be primarily of value as intermediates of use in the preparation of active cephalosporin compounds.

In this specification and the appendant claims the term "lower" in respect of groups containing alkyl moieties, e.g. alkyl, alkoxy or aralkyl, designates groups wherein the alkyl moiety contains 1-6, preferably 1-4 carbon atoms "Lower alkenyl" and "lower alkynyl" refer to $C_2$-$C_7$ groups, while "lower cycloalkyl" refers to $C_5$-$C_7$ groups.

Particularly useful compounds according to the invention include those represented by the general formula

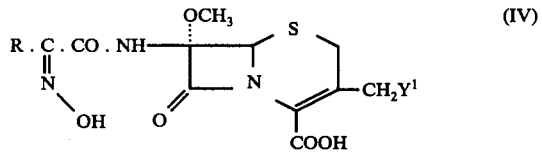

(wherein R is a carbocyclic or heterocyclic aryl group such as phenyl, thienyl and furyl and $Y^1$ is acetoxy or a group $R^6S$- where $R^6$ is a diazolyl, triazolyl, tetrazolyl, thiazolyl, thiadiazolyl, thiatriazolyl, oxazolyl, oxadiazolyl, pyridyl, pyrimidyl, benzimidazolyl, benzoxazolyl, benzothiazolyl, triazolopyridyl or or purinyl group) and non-toxic derivatives thereof. Specific examples of $R^6$ groups which may be present in these compounds include 5-methyl-1,3,4-thiadiazol-2-yl, 1-methyltetrazol-5-yl, 1-ethyltetrazol-5-yl, 1-phenyltetrazol-5-yl, 2-phenyl-1,3,4-oxadiazol-5-yl and 5- and 6-nitrobenzothiazol-2-yl.

Compounds of this type exhibit broad spectrum antibacterial activity against a range of gram positive and gram negative organisms, coupled with high stability to β-lactamases produced by a range of gram negative and staphylococcal organisms and substantial immunity to serum binding.

Specific examples of compounds of the invention include the following:

(6R,7S)-3-acetoxymethyl-7-[2-hydroxyimino-2-(thien-2-yl) acetamido]-7-methoxyceph-3-em-4-carboxylic acid (syn isomer);

6R,7S)-3-acetoxymethyl-7-[2-hydroxymino-2-(fur-2-yl) acetamido]-7-methoxyceph-3-em-4-carboxylic acid (syn isomer);

(6R,7S)-3-acetoxymethyl-7-(2-hydroxyimino-2-phenylacetamido)-7-methoxyceph-3-em-4-carboxylic acid (syn isomer); and (6R,7S)-7-[2hydroxyimino-2-(thien-2-yl)acetamido -7-methoxy-3-(1-methyltetrazol-5-ylthiomethyl)ceph-3-em-4-carboxylic acid (syn isomer).

The compounds according to the invention may be prepared by any convenient method. According to one embodiment of the invention we provide a process for the preparation of a compound of the formula I as hereinbefore defined or a non-toxic derivative thereof, which comprises (A) condensing a compound of the formula

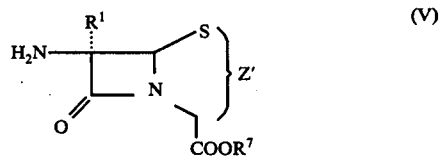

[wherein $R^1$ has the above-defined meaning; $R^7$ is a hydrogen atom or a carboxyl blocking group, e.g. the residue of an ester-forming alcohol (aliphatic or araliphatic), phenol, silanol or stannanol, said alcohol, phenol, silanol or stannanol preferably containing 1-20 carbon atoms, or the residue of an acid; and Z' is a group in which 2 carbon atoms link the nuclear sulphur atom and the carbon atom bearing the carboxylic acid group, preferably so that the compound has $\Delta^2$ or $\Delta^3$ unsaturation] or a salt, e.g. an acid addition salt such as a hydrochloride, hydrobromide, sulphate, nitrate, phosphate, methane sulphonate or tosylate, or an N-silylated derivative thereof with an acylating agent corresponding to the acid

(wherein R has the above-defined meaning) or with an acylating agent corresponding to an acid which is a precursor for the acid (VI); or (B) reacting a compound of the formula

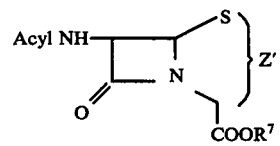

wherein Acyl is the group

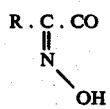

or a precursor therefor and Z' and R⁷ have the above defined meanings) with a $C_{1-4}$ alkoxylating agent (e.g., a lithium base/$C_{1-4}$ alkanol/halogenating agent system) to form the corresponding 7-alkoxide; whereafter, if necessary and/or desired in each instance, any of the following reactions (C) are carried out:

(i) conversion of a precursor for the group

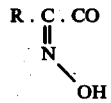

into that said group, (ii) transformation of the group Z' into the desired group Z where these are different, e.g. by conversion of a $\Delta^2$ isomer into the desired $\Delta^3$ isomer and/or by modification or replacement of a substituent atom or group at the 3-position to give the desired 3-position grouping, and (iii) removal of any carboxyl blocking groups, and
(D) recovering the desired compound of formula I if necessary after separation of isomers and if desired after conversion to a non-toxic derivative.

Acylating agents which may be employed in the preparation of compounds of formula I include acid halides, particularly acid chlorides and bromides. Where such acid halides are employed it is generally desirable that they be derived from a precursor of the acid (VI) wherein the hydroxyimino group is O-substituted by protecting group e.g. an easily removable acyl or etherifying group, in order to avoid undesirable side reactions involving the hydroxyimino group. The said protecting group may be removed after the condensation, advantageously in conjunction with the removal of any carboxyl blocking groups, to yield the desired hydroxyimino compound. Suitable precursor acids may thus be represented by the general formula

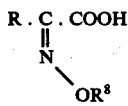 (VII)

wherein R is as defined above and R⁸ is an easily removable acyl or ether group.

Acylations using acid halides may conveniently be effected at temperatures of from −50° to +50° C., e.g. −20° to +30° C. The acylating agent may be prepared by reacting the acid (VII) or a salt thereof with a halogenating agent (e.g. phosphorus pentachloride, thionyl chloride or oxalyl chloride). Use of oxalyl chloride with the sodium or potassium salt of the acid (VII) is preferred since under these conditions syn-anti isomerisation is minimal. The acylation may be effected in aqueous or non-aqueous media and suitable media include an aqueous ketone (e.g. aqueous acetone), an ester (e.g. ethyl acetate), an amide (e.g. dimethylacetamide) a nitrile (e.g. acetonitrile), a halogenated hydrocarbon (eg. methylene chloride) or mixtures thereof.

Acylation with an acid halide may be effected in the presence of an acid binding agent, for example a teriary amine (e.g. pyridine, triethylamine or dimethylaniline), an inorganic base (e.g. calcium carbonate or sodium bicarbonate) or an oxirane such as a lower 1,2-alkylene oxide (e.g. ethylene oxide or propylene oxide), which binds hydrogen halide liberated in the acylation reaction.

Suitable easily removable acyl groups R⁸ which may be present in the acid (VII) and acylating agents derived therefrom include acetyl; acetyl substituted at the α-carbon atom by one or more electron withdrawing groups, as in, for example, trichloroacetyl, dichloroacetyl, monochloroacetyl, trifluoroacetyl, difluoroacetyl and monofluoroacetyl; formyl; diphenylmethoxycarbonyl; benzyloxycarbonyl; t-butoxycarbonyl; and 2,2,2-trichloroethoxycarbonyl. Such groups may be removed by, for example, hydrolytic or reductive cleavage. Thus, for example, an acetyl group may be removed by treatment with aqueous alkali, while halogenated acetyl groups may be removed by treatment with aqueous bicarbonate. Additionally, chloroacetyl can be removed using a nucleophile such as a thiourea. Diphenylmethoxycarbonyl and t-butoxycarbonyl groups can be removed using trifluoroacetic acid, optionally in the presence of anisole, while 2,2,2-trichloroethoxycarbonyl may be removed by means of a reducing agent such as zinc/acetic acid or zinc/formic acid.

Suitable ether groups R⁸ include branched lower alkyl groups such as isopropyl or t-butyl and aralkyl groups such as benzyl, benzyl substituted by one or more methoxy groups, diphenylmethyl and triphenylmethyl, this last group being particularly preferred. Such groups may be cleaved by, for example, acid hydrolysis, e.g. by treatment with trifluoroacetic acid, if desired in the presence of anisole.

Acylation may also be effected with other amide-forming derivatives of acids of formula VI or precursors therefor such as acids of formula VII, such derivatives including, for example, symmetrical anhydrides and mixed anhydrides, e.g. with pivalic acid or formed with a haloformate, e.g. a lower alkylhaloformate. The mixed or symmetrical anhydrides may be generated in situ. For example, a mixed anhydride may be generated using N-ethoxycarbonyl-2-ethoxy-1,2-dihydroquinoline. Mixed anhydrides may also be formed with phosphorus acids (for example phosphoric or phosphorous acids), sulphuric acid or aliphatic or aromatic sulphonic acids (for example p-toluene sulphonic acid). Another convenient acylating agent is an activated ester, e.g. a compound of the formula

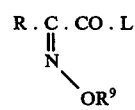 (VIII)

where R has the above-defined meaning, R⁹ is hydrogen or a group as defined for R⁸ in formula VII, and L is an activating group, e.g. azido, oxysuccinimido, oxybenztriazolo, pentachlorophenoxy or p-nitrophenoxy.

Alternatively the free acid form of a compound of formula VI or a precursor therefor, e.g. of formula VII, may be condensed directly with a compound of formula V, the reaction being effected in the presence of a condensing agent. Suitable condensing agents for this purpose include carbodiimides, for example, N,N'-diethyl-, dipropyl- or diisopropylcarbodiimide, N,N'-dicyclohexylcarbodiimide, or N-ethyl-N'-γ-dimethylaminopropylcarbodiimide; a suitable carbonyl compound, for example carbonyldiimidazole; or an isoxazolinium salt, for example, N-ethyl-5-phenylisoxazolinium-3'-sulphonate and N-t-butyl-5-methylisoxazolinium perchlorate. Condensation reactions of this type are desirably effected in an anhydrous reaction medium, e.g. methylene chloride, dimethylformamide or acetonitrile, since one may then regulate more precisely reaction conditions such as temperature.

Compounds of formula I may additionally be prepared by condensation of a compound of formula V with an acylating agent corresponding to an acid of formula

R . CO . COOH     (IX)

(wherein R has the above-defined meaning), whereafter the precursor acyl group R. CO. CO- so introduced is converted to the desired acyl group of formula

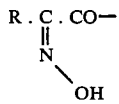

by reaction with hydroxylamine.

Compounds of formula I wherein R is an activating group such as 2- or 4-pyridyl may also be prepared by a technique involving nitrosation. Thus a compound possessing the precursor acylamido group

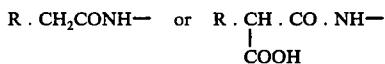

R . CH$_2$CONH—   or   R . CH . CO . NH—
                              |
                             COOH (wherein R is an activating group) may be nitrosated using, for example, nitrous acid (which may be prepared in situ by reaction of an alkali metal nitrite with a weak acid e.g. acetic acid), nitrosyl chloride, or an organic nitrosating agent e.g. an alkyl, cycloalkyl, or aralkyl nitrite. In the case of nitrosation of a compound containing the group

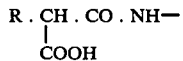

R . CH . CO . NH—
    |
   COOH decarboxylation may occur. Separation of syn and anti-isomers may be necessary after the nitrosation.

As indicated above, the compounds of formula V may if desired by employed in N-silylated form. The use of such N-silylated derivatives in many cases enhances condensation with the acylating agent since the N-silylated derivatives generally have greater solubility in the commonly employed solvent media than the corresponding free 7β-amino compounds so that their use facilitates a smoother and more efficient acylation reaction.

A wide range of silylated derivatives of compounds of formula V may be used, and these may be prepared by any convenient method, advantageously by reaction of the compound V with a halosilane (e.g. trimethylchlorosilane, dimethyldichlorosilane or methyltrichlorosilane) or a silazane (e.g. hexamethyldisilazane).

Where R$^7$ in formula V is a carboxyl blocking group this is desirably a group which may readily be split off at a later stage of the reaction. Suitable blocked carboxyl groups are well known in the art and include aryl lower alkoxycarbonyl groups such as p-methoxybenzyloxycarbonyl, p-nitrobenzyloxycarbonyl or diphenylmethoxycarbonyl, lower alkoxycarbonyl groups such as t-butoxycarbonyl and lower haloalkoxycarbonyl groups such as 2,2,2-trichloroethoxy carbonyl. The carboxyl blocking group may subsequently be removed by any of the usual methods, for example, acid-and base-catalysed hydrolysis is generally applicable, as are enzymically-catalysed hydrolyses.

Where the resultant compound is a ceph-2-em-4-ester the desired ceph-3-em compound may be obtained by treatment of the former with a base.

The acid of formula VI to which the acylating agent corresponds may be obtained by known methods, e.g. by the techniques described in our Belgian Pats. Nos. 778630 and 783449.

The 7α-alkoxy-7β-amino cephalosporin starting materials of formula V may be prepared by any convenient method, e.g. as described in the literature. Thus, for example, compounds of formula V may be prepared as described in Belgian Pat. No. 768528 or in Dutch published Patent Application No. 7204982, or by the N-deacylation of fermentationproduced 7β-acylamido-7α-methoxy cephalosporins or the ring expansion of 6α-alkoxypenicillin sulphoxides. The compounds of formula I and starting materials of formula V may also be prepared by techniques involving the methods described in J. Amer. Chem. Soc. 1973, 95, 2401-3 and 2403-4, J. Org. Chem. 1973, 38, 2857, and Tetrahedron Letters 1973, No. 4, 273-6.

Compounds of formula V generally do not exhibit particularly high stability and are therefore desirably acylated to introduce the desired 7β-acylamido group or a precursor therefor directly following their preparation.

The compounds according to the invention may be distinguished by appropriate techniques, e.g. by their ultraviolet spectra, by thin layer or paper chromatography or by their nuclear magentic resonance spectra. For example, for DMSO-d$_6$ solution compounds of formula I exhibit the doublet for the amide NH at a lower field for the syn isomers than for the anti-isomers. These factors may be employed in monitoring reactions.

Non-toxic derivatives of compounds of formula I may be formed in any convenient way. Thus, for example, base salts may be formed by reaction of the cephalosporin acid with sodium or potassium 2-ethylhexanoate.

The antibacterial compounds according to the invention may be formulated for administration in any convenient way, by analogy with other antibiotics and the invention therefore includes within its scope a pharmaceutical composition comprising an antibacterial compound of formula I or a non-toxic derivative e.g. salt thereof (as herein defined) adapted for use in human or veterinary medicine. Such compositions may be presented for use in conventional manner with the aid of any necessary pharmaceutical carriers or excipient.

For veterinary medicine the composition, may, for example, be formulated as an intramammary preparation in either long acting or quick-release bases.

The compositions may contain from 0.1% upwards, preferably from 10–60% of the active material, depending on the method of administration. Where the compositions comprise dosage units, each unit will preferably contain 50–500 mg of the active ingredient. The dosage as employed for adult human treatment will preferably range from 100 to 3000 mg per day, for instance 1500 mg per day, depending on the route and frequency of administration.

The compounds according to the invention may be administered in combination with other therapeutic agents such as antibiotics, for example other cephalosporins, the penicillins or tetracyclines.

The following examples illustrate the invention.

The following procedures were adopted unless specified otherwise:

Melting-points were determined in glass capillaries and are uncorrected. Optical rotations were measured in chloroform solution between 18 and 25° at concentrations of 1 ± 0.3%. Paper chromatography was performed on Whatman No. 1 paper in 4:1:5=butan-1-ol:ethanol:water. Thin-layer chromatography was performed on Merck precoated silica gel plates in 9:1=benzene:ethyl acetate. Ultraviolet spectra were measured in ethanol solution. Organic solutions were dried over anhydrous magnesium sulphate; solids were dried in vacuo at +20°. Methylene chloride and 1,4-dioxan were dried by passage through Woelm grade I basic alumina. Chromatography with silica gel refers to the use of Merck 70–230 mesh kieselgel. Kieselgel G refers to the t.l.c. grade Merck variety. All temperatures are indicated in degrees centigrade. The structure of each of the compounds prepared was verified by p.m.r. spectroscopy (all compounds), i.r. spectroscopy (except for the compound of Preparation I(c), and microanalysis (except for the compounds of Example 3(b) and Preparations 1(a) and 1(c)).

Preparation 1 t-Butyl (6R,7S)-3-acetoxymethyl-7-amino-7-methoxyceph-3-em-4-carboxylate (a) Sodium nitrite (2.70 g, 39 mmole) was added to a cold (0° to +5°), stirred mixture of t-butyl (6R7R)-3-acetoxymethyl-7-aminoceph-3-em-4-carboxylate (6.65g, 20.1 mmole), 2N-sulphuric acid (14.7 ml, 29.4 mmole), water (400 ml) and methylene chloride (400 ml). The mixture was stirred for one hour at 0° to +5° and the phases were then separated. The aqueous layer was washed with methylene chloride (100 ml) and the combined organic layers were dried and concentrated at +15° to +20° to ca 125 ml.

During this diazotisation, solutions of triethylammonium azide and bromine azide were prepared as follows: sodium azide (11.7 g, 180 mmole) was added to a cold (0° to +5°), stirred mixture of conc. sulphuric acid (9.7 ml) water (80 ml) and methylene chloride (190 ml), and stirring was continued for 30 minutes at 0° to +5°. The phases were separated by decantation and the aqueous layer was washed with methylene chloride (10 ml). The combined organic layers were dried and divided into two equal portions. To one portion was added triethylamine (4.9 ml, 35 mmole) and to the second portion was added N-bromosuccinimide (4.93 g, 27.7 mmole). The two solutions were stored at 0° to +5° until used.

The diazotisation solution was cooled to −40° under a dry nitrogen atomosphere and stirred while the solution of triethylammonium azide was added. The bromine azide solution was then added over 5 minutes at −25 to −30° and the mixture then allowed to warm to 0° over 20 minutes. The solution was washed with a solution of disodium hydrogen phosphate (10 g.) in water (300 ml), and then dried and evaporated to a yellow foam. Chromatography on silica gel (125 g) in benzene gave t-butyl(6R,7R and S[5:1])-3-acetoxymethyl-7-azido-7-bromoceph-3-em-4-carboxylate as a yellow oil (2.960 g, 6.85 mmole, 34%), $\lambda_{max}$ 252.5 nm, inflexion at 266 nm, ($\epsilon$ 7,650 and 7,400 respectively). The n.m.r. spectrum indicated the assigned isomer ratio.

A further reaction in which the diazotisation solution was not concentrated afforded the product in 58% yield.

(b) A solution of t-butyl (6R,7R and S[5:1])-3-acetoxymethyl-7-azido-7-bromoceph-3-em-4-carboxylate (17.255 g, 39.8 mmole), pyridine (3.24 ml, 40 mmole), silver tetrafluoroborate (8.55 g, 43.8 mmole) in methylene chloride (160 ml), and methanol (320 ml) was stirred at +20° to +25° for 16 hours (a grey precipitate appeared within 1 to 2 minutes, but t.l.c. indicated that the long reaction-time was necessary). The mixture was filtered through Celite and the filtrate was evaporated and chromatographed on silica gel (250 g) in 5% ethyl acetate in benzene. A mixture of t-butyl (6R,7R and S[1:5])-3-acetoxymethyl-7-azido-7-methoxyceph-3-em-4-carboxylates was obtained as a pale-yellow viscous oil which slowly crystallised (13.910 g, 36.2 mmole, 90.5%), $\lambda_{max}$ 248.5 nm, inflexion at 265 nm ($\epsilon$7,500 and 7,060 respectively). The n.m.r. spectrum indicated the assigned isomer ratio. Crystallisation of a sample from ether and petroleum-ether (b.p. 60° to 80°) provided a sample of t-butyl(6R,7S)-3-acetoxymethyl-7-azido-7-methoxyceph-3-em-4-carboxylate as a white crystalline solid m.p. 77.5° to 78.5°(dec); $[\alpha]_D$ −33.2°; t.l.c. $R_f$ 0.51: $\lambda_{max}$ 247.5 nm, inflexion at 264.5 nm ($\epsilon$ 8,180 and 7,600 respectively). c)(i) A suspension of platinum oxide (99.4 mg) in dry dioxan (10 ml) was stirred under a dry nitrogen atmosphere. A slow stream of hydrogen was then bubbled through the suspension for 3 minutes. A solution of t-butyl (6R,7S)-3-acetoxymethyl-7-azido-7-methoxyceph3-em-4-carboxylate (98.7 mg, 0.257 mmole) in dry dioxan (5 ml) was added to the suspension and stirring continued for a total of 25 hours; the stream of hydrogen was passed for the first 7½ hours and the last 2 hours of this period. The black solution-suspension was stirred with charcoal (2 g) for 10 minutes and then filtered through a bed of charcoal on kieselgel G (Merck) on Celite. The filtrate was evaporated to give a crude sample of the title compound, t.l.c. $R_f$ 0.13.

(ii) In larger-scale reductions, the 5:1 mixture of t-butyl (6R,7S and R respectively)-3-acetoxymethyl7-azido-7-methoxyceph-3-em-4-carboxylate from (b) above was used without further purification. The reduction was accelerated by using 1 weight-equivalent of platinum oxide with a hydrogen pressure of 2.5 to 3 atmosphere for 1 hour, then a further 0.25 weight-equivalent of platinum oxide with a hydrogen pressure of 2.5 to 3 atmosphere for 40 minutes; after this time the reduction was complete. The mixture was filtered through paper and the residual platinum recovered. The reaction solution still contained colloidal platinum but was evaporated and used without further purification.

Preparation 2

2-Triphenylmethoxyimino-2-(thien-2-yl)acetyl chloride (syn isomer)

(a) 2-Hydroxyimino-2-(thien-2-yl)-acetic acid (syn isomer) (2.5106 g, 14.68 mmole), triphenylmethyl chloride (6.122 g, 21.95 mmole) and triethylamine (5 ml, 36.4 mmole) in dry methylene chloride (50 ml) were stirred at 0° for 30 minutes. The mixture was washed with 2N-hydrochloric acid (50 ml), water (50 ml), then dried and evaporated to a yellow oil. The solution of this oil in ether (30 ml) was stirred whilst triethylamine (2.5 ml, 18.2 mmole) was added. Triethylammonium 2-triphenylmethoxyimino-2-(thien2-yl)acetate (syn isomer) crystallised out immediately and was stirred at 0 to +5° for 5 minutes and then isolated by filtration, washed with ether, and dried to a white powder (7.28 g, 14.15 mmole, 96%) m.p. 161 to 168° (dec); $\lambda_{max}$260, 267.5 and 290.5 nm ($\epsilon$9,000; 8,900 and 11,470 respectively).

(b) A solution of triethylammonium 2-triphenylmethoxyimino-2-(thien-2-yl)-acetate (syn isomer) (2.30 g, 4.46 mmole) in dry methylene chloride (50 ml) was cooled to 0° to +5° and stirred whilst oxalyl chloride (0.38 ml, 4.46 mmole) was added. N,N-Dimethylformamide (ca 0.1 ml) was added and the mixture was stirred at 0° to +5° for 2½ hours. The solvent was evaporated and the residue was stirred with ether (100 ml) for 1 hour, and the suspension then filtered. The filtrate and ether washings (100 ml) were evaporated to give the title compound as a white crystalline solid (1.985 g, quantitative). This acid chloride was used without further purification.

Preparation 3

2-Triphenylmethoxyimino-2-(fur-2-yl)acetyl chloride (syn isomer)

(a) Triethylamine (35 ml, 250 mmole), triphenylchloromethane (35 g, 125 mmole) and 2-hydroxyimino-2-(fur-2-yl)-acetic acid (syn isomer) 15.505 g, 100 mmole) were reacted together essentially as described in Preparation 2(a) to give triethylammonium 2-triphenylmethoxyimino-2-(fur-2-yl) acetate (syn isomer) as a pale-yellow solid (39.5 g, 79 mmole, 79%), m.p. 170° to 172° (dec), $\lambda_{max}$275.5 nm, inflexions at 265 and 271.5 nm ($\epsilon$ 17,900; 15,900 and 17,500 respectively). (b) The title compound was prepared from the product of (a) above essentially as described in Preparation 2(b) and used without further purification in Example 2.

Preparation 4

2-Triphenylmethoxyimino-2-phenylacetyl chloride(syn isomer)

(a) 2-Hydroxyimino-2-phenylacetic acid (syn isomer) (4.13 g, 25.0 mmoles), triethylamine (8.7 ml, 62.5 mmoles) and triphenylchloromethane (10.40 g, 37.5 mmoles) were reacted together as described in Preparation 2(a) to give triethylammonium 2-triphenylmethoxyimino-2-phenylacetate (syn isomer) as a white solid (10.625 g, 21 mmole, 84%) m.p. 166 to 175 (dec), $\lambda_{max}$260 nm, inflexions at 264 and 292 nm ($\epsilon$15,000; 14,400 and 2,300 respectively).

(b) The title compound was prepared from the product of (a) above (10 mmole) by the procedure described in Preparation 2(b) and used without further purification in Example 3.

EXAMPLE 1

(a) t-Butyl (6R,7S)-3-Acetoxymethyl-7-methoxy-7-[2-triphenylmethoxyimino-2-(thien-2-yl)-acetamido]-ceph-3-em-4-carboxylate (syn isomer)

(i) A solution of t-butyl (6R,7R and S)-3-acetoxymethyl-7-amino-7-methoxyceph-3-em-4-carboxylate [prepared in accordance with Preparation 1(c)(ii) from 3.90 mmole of the corresponding 7-azido-7-methoxy compound] in dry methylene chloride (50 ml) was stirred and cooled to 0 to +5°. Pyridine (0.63 ml, 7.80 mmole) was added, followed by a solution of 2-triphenylmethoxy-imino-2-(thien-2-yl)-acetyl chloride (syn isomer) (prepared from 4.46 mmole of the corresponding acid triethylamine salt as described in Preparation 2) in dry methylene chloride (10 ml). The reaction was stirred at 0 to 5° for 23½ hours and washed successively with 0.5N-hydrochloric acid (50 ml), water (50 ml), water-saturated sodium bicarbonate (1:1, 50 ml) then dried and evaporated to a dark oil. Chromatography of this oil on kieselgel G (150 g) in 5:1 =benzene:ethyl acetate provided a sample of the title compound as a yellow foam 253 mg, 0.34 mmole, 8.7%), $[\alpha]_D+44°$, $\lambda_{max}$ 264.nm, inflexion at 286.5 nm ($\epsilon$ 15,000 and 13,250 respectively).

(ii) A solution of t-butyl (6R,7R and S)-3-acetoxymethyl 7-amino-7-methoxyceph-3-em-4-carboxylate [prepared in accordance with Preparation 1 (c) (ii) from 12.00 mmole of the corresponding 7-azido-7-methoxy-compound]in dry methylene chloride (150 ml) was stirred and cooled to 0° to +5°. Pyridine (0.97 ml, 12.00 mmole) was added, followed by trimethylsilyl chloride (1.54 ml, 12.00 mmole). The mixture was stirred and allowed to warm to +20° over 30 minutes, then cooled to 0° to 5°. Further pyridine (0.97 ml, 12.00 mmole) was added and then a solution of 2-triphenylmethoxyimino-2-(thien-2-yl)-acetyl chloride (syn isomer) (prepared from 13.00 mmole of the corresponding acid-triethylamine salt as described in Preparation 2) in dry methylene chloride (30 ml) was added. The mixture was stirred and allowed to warm to +20° over 2½ hours, then worked up and chromatographed as in (i) above to give the title compound (730 mg, 0.97 mmole, 8%). The i.r. and n.m.r. spectra and t.l.c. behaviour of this product resembled those of the product isolated in part (i) above. Fractions eluted just before those above were evaporated to give a further amount of less pure title compound (1.110 g, ca 1.45 mmole, 12%). The t.l.c. behaviour and n.m.r. spectrum showed that this batch of product contained 20 to 30% of t-butyl (6R,7R)-3-acetoxymethyl-7-methoxy-7-[2-triphenylmethoxyimino-2-(thien-2-yl) acetamido]-ceph-3-em-4-carboxylate (syn isomer).

(b) (6R,7S)-3-Acetoxymethyl-7-[2-hydroxyimino-2-(thien-2-yl)-acetamido]-7-methoxyceph-3-em-4-carboxylic Acid (syn isomer)

t-Butyl (6R,7R and S [ca 1:8])-3-acetoxymethyl-7-methoxy-7[2-triphenylmethoxyimino-2-(thien-2-yl)-acetamido]-ceph-3-em-4-carboxylate (1.172 g, 1.56 mmole) was stirred with anisole (1.5 ml) and trifluoroacetic acid (5 ml) for 1 hour at +20°. The solution was added dropwise to vigorously stirred saturated aqueous sodium bicarbonate solution (400 ml); the mixture was stirred for 10 minutes and then washed with ethyl acetate (3×80 ml). The aqueous layer was covered with ethyl acetate (80 ml) and adjusted to pH 3 with orthophosphoric acid. The aqueous layer was extracted with ethyl acetate (3×80 ml) and the combined ethyl acetate layers were washed with brine, then passed through Whatman 1 PS phase-separating paper and evaporated. The residual foam was chromatographed on kieselgel G (60 g) in 4:1:5 butan-1-ol:ethanol:water. The appropriate fractions were combined and evaporated and the residue was dissolved in acetone, filtered through Celite, and evaporated to provide the title compound as a pale-brown amorphous solid containing 0.8 mole butan-1-ol, and 0.07 mole acetone (nmr) and 5 mole water (416 mg, 0.66 mole, 42.5%), paper chromatography Rf/Rf cephaloram 0.84, $[\alpha]_D+40°$ (Me$_2$SO), $\lambda_{max}$(pH 6-buffer)

264.5 nm, inflexion at 290 nm (ε 15,200 and 10,700 respectively).

EXAMPLE 2

(a) t-Butyl (6R,7S)-3-Acetoxymethyl-7-methoxy-7-[2-triphenylmethoxyimino-2-(fur-2-yl)-acetamido]-ceph-3-em-4-carboxylate (syn isomer)

An acylation similar to that described in Example 1(a) (i) with the same 7-amino-7-methoxy ester (from 0.555 mmoles of the corresponding 7-azido-7-methoxy ester), 2-triphenylmethoxyimino-2-(fur-2-yl)-acetyl chloride (syn isomer) (1 mmole) and pyridine (2.17 mmole) provided the title compound as a foam (120.9 mg, 0.164 mmole, 29.5%), tlc Rf (benzene:ethyl acetate = 3:1) 0.83, $[\alpha]_D +46°$, $\lambda_{max}$ 281 nm (ε 21,2000).

A further experiment similar to that described in Example 1(a)(ii) but with 2-triphenylmethoxyimino-2-(fur-2-yl)acetyl chloride (syn isomer) gave the title compound in 24.8% yield.

(b) (6R,7S)-3-Acetoxymethyl-7-[2-hydroxyimino-2-(fur-2-yl) acetamido]-7-methoxyceph-3-em-4-carboxylic Acid (syn isomer)

t-Butyl (6R,7S)-3-acetoxymethyl-7-methoxy-7-[2-triphenylmethoxyimino-2-(fur-2-yl)-acetamido]-ceph-3-em-4-carboxylate (syn isomer) (713.3 mg, 0.966 mmole) was treated with trifluoroacetic acid (10 ml) and anisole (5 ml) for a total of 40 mins. and then added slowly to rapidly stirred saturated aqueous sodium bicarbonate (600 ml.). The mixture was extracted with ethyl acetate (2×150 ml), covered with ethyl acetate (200 ml), and adjusted to pH 2 with orthophosphoric acid. The organic layer was combined with the ethyl acetate wash (200 ml) of the aqueous layer, dried, and evaporated to a brown foam. Chromatography on three 40 × 20 cm. preparative-layer plates in chloroform-methanol-formic acid (90:16:2) provided a sample of the title compound as a pale-yellow foam containing ca 2½mole-equivalents water (i.r. and microanalysis) (137 mg, 0.283 mmole, 29%) paper chromatography Rf 0.26, Rf$_{/Rfcephaloram}$ 0.58, $\lambda_{max}$ (pH 6 buffer) 272.5 nm (ε 16,400).

EXAMPLE 3

(a) t-Butyl (6R,7S)-3-Acetoxymethyl-7-methoxy-7-[2-triphenylmethoxyimino-2-phenylacetamido]-ceph-3-em-4-carboxylate (syn isomer)

An acylation similar to that described in Example 1(a)(ii) with the same 7-amino-7-methoxy ester (from 10 mmole of the corresponding 7-azido-7-methoxy ester), pyridine (2.02 ml, 25 mmole) and trimethylsilyl chloride (1.28 ml, 10 mmole) and then 2-triphenylmethoxyimino-2-phenylacetyl chloride (syn isomer) (10 mmole) and pyridine (2.02 ml, 25 mmole) provided the title compound as a yellow foam containing ½ mole-equivalent of toluene (chromatography co-solvent) (490 mg, 0.617 mmole, 6.2%); tlc Rf (toluene: ethyl acetate=3:1) 0.55 (the starting amine has an Rf in this system of ca 0.30), $[\alpha]_D + 19°$, $\lambda_{max}$ 262 nm, inflexions at 265.5 and 294 nm (ε 20,100; 20,000 and 4,900 respectively).

(b) Sodium (6R,7S)-3-Acetoxymethyl-7-[2-hydroxyimino-2-phenylacetamido]-7-methoxyceph-3-em-4-carboxylate (syn isomer)

t-Butyl (6R,7S)-3-acetoxymethyl-7-methoxy-7-[2-triphenylmethoxyimino-2-phenylacetamido]-ceph-3-em-4-carboxylate (syn isomer) (400 mg, 0.535 mmole) was treated with anisole (2 ml) and trifluoroacetic acid (8 ml) as described in Example 1(b) to give (6R,7S)-3-acetoxymethyl-7-[2-hydroxyimino-2-phenylacetamido]-7-methoxyceph-3-em-4-carboxylic acid (syn isomer) as an electrostatic white solid. (135 mg, 0.30 mmole). This acid was converted into the title compound by dissolving it in water containing sodium bicarbonate (25 mg, 0.298 mmole), filtering the solution and freeze-drying the filtrate to give the product as an amorphous solid (120 mg, 0.255 mmole, 51%), paper chromatography Rf 0.40 Rf$_{/Rfcephaloram}$ 0.78, $\lambda_{max}$ (pH6 buffer) 254 nm (ε 10,400).

EXAMPLE 4 cl (a) Diphenylmethyl (6R,7R)-3-(1-Methyltetrazol-5-ylthiomethyl)-7-[2-triphenylmethoxyimino-2-(thien-2-yl)acetamido]ceph-3-em-4-carboxylate(syn isomer)

2-Triphenylmethoxyimino-2-(thien-2-yl)acetyl chloride (syn isomer) (1.008g, 2.34 mmole) was dissolved in dry methylene chloride (15 ml) and the solution was added dropwise over 10 minutes to a stirred and cooled (0°) solution of diphenylmethyl (6R,7R)-7-amino-3-(1-methyl-tetrazol-5-ylthiomethyl)ceph-3-em-4-carboxylate (2.472g, 5 mmole) and propylene oxide (DL-2-methyloxiran) (2.5 ml) in methylene chloride (50 ml). Stirring was continued for a further hour, when the solution was washed successively with 2 N-hydrochloric acid, saturated sodium bicarbonate and brine (30 ml of each) and dried, and the solvent was evaporated off. The residual foam (3.65g) was purified by chromatography on kieselgel (80g) with toluene: ethyl acetate = 10:1 as eluant. Fractions with Rf ca 0.6 (tlc, toluene: ethyl acetate = 2:1 for development) were combined and evaporated to dryness in vacuo and the residue, in methylene chloride solution, was run into petroleum ether (b.p. 40-60°) to give the title ester (1.49g, 71%) as a colourless amorphous solid, $[\alpha]_D - 116°$; $\lambda_{max}$ 265nm ($E_{1cm}^{1\%}$ 200) and 290nm ($E_{1cm}^{1\%}$ 202).

(b) Diphenylmethyl (6R,7S)-7-[2-triphenylmethoxyimino-2-(thien-2-yl)acetamido]-3-(1-methyltetrazol-5-ylthiomethyl)-ceph-3-em-4-carboxylate(syn isomer)

A precooled (−70°) solution of diphenylmethyl (6R,7R)-3-(1-methyltetrazol-5-ylthiomethyl)7-[2-triphenyl-methoxyimino-2-(thien-2-yl)acetamido]ceph-3-em-4-carboxylate (syn isomer) (1.409g, 1.58 mmole) in dry tetrahydrofuran (6ml) was added dropwise over 1 minute to a stirred and cooled (−70°) solution of lithium methoxide (210 mg. 3.5 equivs) in dry methanol (6ml) and tetrahydrofuran (40 ml). The reaction was carried out under dry nitrogen. After stirring for 1 minute, t-butyl hypochlorite (0.38 ml, 2 equivs) was added in one batch. After stirring for a further 5 minutes the reaction mixture was poured into a stirred mixture of ethyl acetate (50 ml) and water (200 ml) containing ammonium chloride (ca 5g), and sodium metabisulphite (ca 2.5g). Separation of the phases and removal of the solvent yielded the crude title ester which was purified by crystallisation from methylene chloride: petroleum ether (b.p. 40°-60° ) to give the title ester (583 mg,40%); Rf 0.3(tlc, toluene: ethyl acetate = 5:1 for development); $[\alpha]_D - 44°$; $\lambda_{max}$ 265nm ($E_{1cm}^{1\%}$ 150) and 293.5nm ($E_{1cm}^{1\%}$ 165).

(c)
(6R,7S)-7[2-hydroxyimino-2-(thien-2-yl)acetamido]-7-methoxy-3-(1-methyltetrazol-5-ylthiomethyl)ceph-3-em-4-carboxylic Acid (syn isomer)

The ester described in (b) above (520 mg, 0.565 mmole) was suspended in a mixture of trifluoroacetic acid (2ml) and anisole (0.5ml) and the mixture was kept at 0° for 5 minutes, during which time the solid all dissolved. The resulting solution was poured into iced water (100ml), ethyl acetate (50ml) was added, and saturated sodium bicarbonate was added with stirring to adjust the pH of the solution to 8. The alkaline solution was run off and covered with ethyl acetate (300ml) and acidified to pH 2 with 2N-hydrochloric acid. The organic phase was separated, washed with water and brine(50ml of each) and dried, and the solvent was evaporated off. The residue was dissolved in acetone (25ml), the solution was treated with charcoal and the mixture filtered through kieselguhr. The filtrate was evaporated to dryness in vacuo and the residue, in ethyl acetate solution, was run into petroleum ether (b.p. 40°-60°) to give the title acid (190mg,66%) as a pale-yellow amorphous solid, Rf/Rf cephalothin 0.9; $[\alpha]_D^{22} - 67.5°$ (c 0.86, acetone); $\lambda_{max}$(0.1M-pH6 phosphate buffer(272nm ($\epsilon$15,400). This product was contaminated with the anti isomer (ca 10%) as evidenced by paper chromatography(Rf/Rf cephalothin 1.2) and high pressure liquid chromatography.

I claim:

1. A compound selected from the group consisting of a compound of the formula:

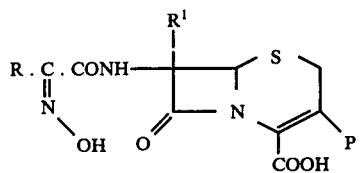

wherein R is phenyl, thienyl or furyl; $R^1$ is $C_1$-$C_4$ alkoxy; P is a group —$CH_2Y$ wherein Y is —$OCOR^9$ or —$OCOAR^{10}$ where A is O, S or NH, $R^9$ is methyl and $R^{10}$ is hydrogen or $R^9$; which is the syn isomer or a mixture of syn and anti isomers containing at least 75% of the syn isomer and a physiologically acceptable salt thereof.

2. The compound of claim 1, which is (6R, 7S)-3-acetoxymethyl-7-[2-hydroxyimino-2-(thien-2-yl)acetamido]-7-methoxyceph-3-em-4-carboxylic acid (syn isomer).

3. The compound of claim 1 which is (6R, 7S)-3-acetoxymethyl-7-[2-hydroxyimino-2-(fur-2-yl)acetamido]-7-methoxy-ceph-3-em-4-carboxylic acid (syn isomer).

4. The compound of claim 1 which is (6R, 7S)-3-acetoxymethyl-7-(2-hydroxyimino-2-phenylacetamido)-7-methoxy-ceph-3-em-4-carboxylic acid (syn isomer).

* * * * *